United States Patent

Kawaguchi et al.

[11] Patent Number: 5,571,040
[45] Date of Patent: Nov. 5, 1996

[54] METHOD AND DEVICE FOR DETECTING BLADE FLEXURE AND BLADE FLEXURE CONTROL DEVICE FOR USE WITH A SLICING MACHINE

[75] Inventors: Keishi Kawaguchi, Higashihiroshima; Tatsumi Hamasaki, Hiroshima; Yoshihiro Tadera, Kure; Kunio Matsuda, Aki-gun, all of Japan

[73] Assignee: Toyo Advanced Technologies Co., Ltd., Hiroshima-ken, Japan

[21] Appl. No.: 168,023

[22] Filed: Dec. 15, 1993

[30] Foreign Application Priority Data

Jan. 18, 1993 [JP] Japan ................................. 5-006087
Oct. 5, 1993 [JP] Japan ................................. 5-248953

[51] Int. Cl.⁶ .................................................. B24B 49/00
[52] U.S. Cl. .............................. 451/11; 451/180; 451/5
[58] Field of Search ........................... 451/11, 180, 14, 451/5, 26, 72; 125/13.02, 12, 13.01; 83/72, 74

[56] References Cited

U.S. PATENT DOCUMENTS

| 4,228,782 | 10/1980 | Demers et al. ............... 125/13.02 |
| 4,420,909 | 12/1983 | Steere, Jr. ..................... 125/13.02 |
| 4,502,459 | 3/1985 | Dyer .............................. 125/13 R |
| 4,653,361 | 3/1987 | Zobeli ........................... 451/11 |
| 4,844,047 | 7/1989 | Brehm et al. .................. 125/20 |
| 4,991,475 | 2/1991 | Malcok et al. ............... 125/13.02 |
| 5,025,593 | 6/1991 | Kawaguchi et al. ......... 451/11 |
| 5,174,270 | 12/1992 | Katayama et al. ........... 125/20 |
| 5,287,843 | 2/1994 | Katayama et al. ........... 451/11 |
| 5,313,741 | 5/1994 | Toyama ......................... 451/11 |

*Primary Examiner*—D. S. Meislin
*Assistant Examiner*—Derris H. Banks
*Attorney, Agent, or Firm*—Jordan and Hamburg

[57] ABSTRACT

A method and device are adapted for detecting and controlling the flexure of a flat ring blade member of a slicing machine in which a workpiece is placed in the blade member, and a relative movement is rendered between the blade member being rotated and a workpiece in a radial direction of the blade member to produce a wafer of the workpiece. An axial load acting between the workpiece and the blade member is detected. A flexure amount of the blade member is calculated on the basis of the axial load detected. The flexure of the blade member is corrected on the basis of the flexure amount calculated.

19 Claims, 14 Drawing Sheets

FIG. 9A
FIG. 9B
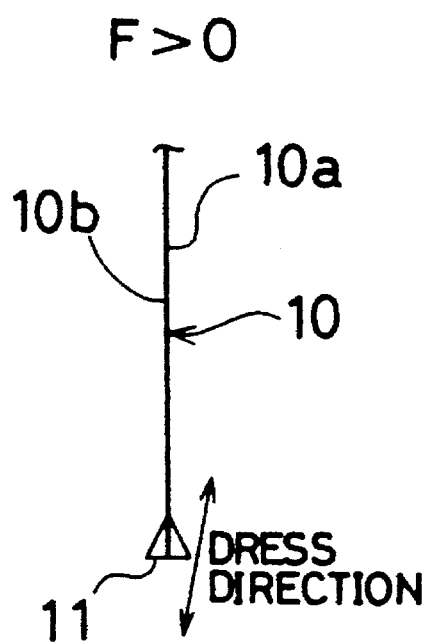
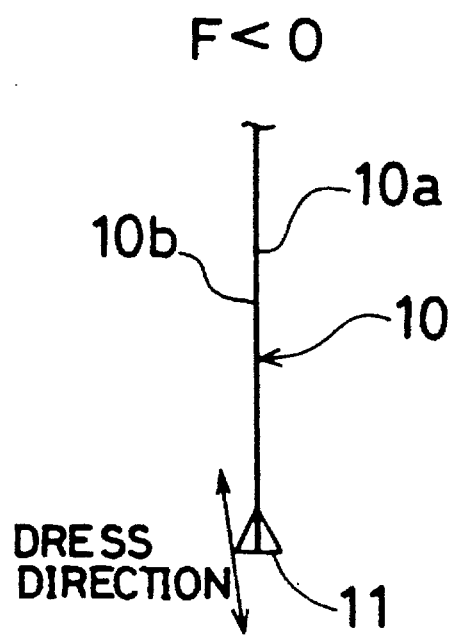

METHOD AND DEVICE FOR DETECTING BLADE FLEXURE AND BLADE FLEXURE CONTROL DEVICE FOR USE WITH A SLICING MACHINE

BACKGROUND OF THE INVENTION

1. Field of the Invention

The present invention relates generally to a slicing machine equipped with a rotatable, flat, circular, ringed blade member having an internal cutting edge at an internal circumferential periphery thereof, wherein the internal cutting edge slices a workpiece made of semiconductor ingot or the like material to produce a wafer. More specifically, the present invention relates to a method and a device for detecting the flexure for use with this type of slicing machine and also to a flexure control device.

2. Description of the Prior Art

A slicing mechanism of such slicing machines is generally characterized in that a workpiece is placed in a central hole of a flat, circular, ringed blade member so as to slightly cross over the internal cutting edge in an axial direction of the blade member, and is shifted against the internal cutting edge in a radial direction of the blade member rotating to produce a wafer. Such a slicing machine is likely to cause a flexure of the blade member during cutting operation. This inherence of this kind of slicing machine may induce deterioration of machining accuracy due to undesirable flexure. To compensate the deterioration in the machining accuracy, detection of flexure has been conventionally attempted in various ways as shown in, for example, Unexamined Japanese Utility Model Publication No. 62-70904, Unexamined Japanese Patent Publication No. 1- 182015.

FIG. 14 shows one of these conventional techniques for detecting the flexure. In the drawing, a flexure detecting sensor 29 is provided near a shifting zone C, along which a workpiece 30 moves in a direction of an arrow A, as close as possible without overlapping with this shifting zone C. This shifting zone C ranges from an inlet side P1 to an outlet side P2 of an internal cutting edge 11 of the blade member 10 in its widthwise direction. The flexure detecting sensor 29 is close to the inlet side P1, i.e., an upstream side of a rotational direction B of a flat, circular, ringed blade member 10. On the basis of a flexure amount detected by the flexure detecting sensor 29, an adjustment on overall flexure of the blade member 10 is performed in the axial direction of the blade member 10.

During slicing operation, contact between the flat, circular, ringed blade member 10 and the workpiece 30 to be sliced is longest at a midway point P3 of the shifting zone C. In other words, flexure occurring in this midway point P3 causes adverse affection to machining accuracy of the workpiece 30 most seriously. It is, thus, desirable to locate the above flexure detecting sensor 29 at a position closer to the shifting zone C, especially to a position corresponding to the midway point P3. However, interference between the flexure detecting sensor 29 and the workpiece 30 must be avoided. Accordingly, the position where the flexure detecting sensor 29 is installed needs to be out of the shifting zone C being offset far away from the midway point P3, as shown in FIG. 14. This inevitable offset from the midway point P3 results in a problem that an overall adjustment on flexure of the blade member 10 cannot be done accurately or properly.

To solve this problem, there has been recently proposed a detecting technique, as disclosed in Unexamined Japanese Patent Publication No. 4-138210. According to this prior art, a flexure detecting sensor of eddy current type is disposed at a position confronting with the front end surface of a workpiece to be machined so as to detect a flexure amount of the central portion of the workpiece through a wafer produced being cut off from the workpiece. This detecting technique is advantageous in that the flexure detecting sensor can be disposed near the central portion of the workpiece because interference between the workpiece and the flexure detecting sensor can be surely avoided.

However, a problem of this type detecting technique resides in that the flexure amount is indirectly detected. More specifically, the wafer is interposed between the workpiece and the flexure detecting sensor; therefore, the flexure amount detected will reflect a significant amount of affection by the wafer. Some of the workpieces have electric resistances comparable with conductors. Furthermore, the thickness or size of the wafer produced from the workpiece is not always constant, rather varies depending on slicing condition. Due to such size dispersion of the wafer, it is normally difficult to accurately detect the flexure amount of the blade member on the basis of the value measured by the flexure detecting sensor.

SUMMARY OF THE INVENTION

Accordingly, the present invention has an object, in view of the above problems, to provide a method and a device for detecting the flexure which make it possible to accurately detecting the flexure of a blade member at a portion most sensitive to the flexure in a slicing machine without increasing structural complicatedness, and further to provide a flexure control device capable of utilizing a flexure amount detected by the above detecting method or device.

In accordance with a first aspect of the present invention, there is provided a method for detecting a flexure of a blade member of a slicing machine in which a workpiece is placed in the blade member in the form of a flat ring and having an internal cutting edge on an internal periphery thereof, and a relative movement is rendered between the blade member being rotated and a workpiece in a radial direction of the blade member to produce a wafer of the workpiece, the detecting method comprising the steps of: detecting an axial load acting between the workpiece and the blade member; and calculating a flexure amount of the blade member on the basis of the axial load.

With thus detecting method, the axial load acting between the workpiece and the blade member is detected first of all. Then, on the basis of the axial load detected, a flexure amount of the blade member is calculated in accordance with a specified relationship between an axial load acting in an axial direction of the workpiece and a flexure amount of the blade member. This detection of flexure amount is accurate compared with the conventional method of using an eddy current type sensor indirectly detecting the flexure amount through a wafer.

A second aspect of the present invention provides a method for controlling the flexure of a blade member of a slicing machine in which a workpiece is placed in the blade member in the form of a flat ring and having an internal cutting edge on an internal periphery thereof, and a relative movement is rendered between the blade member being rotated and a workpiece in a radial direction of the blade member to produce a wafer of the workpiece, the controlling method comprising the steps of: detecting an axial load acting between the workpiece and the blade member; calculating a flexure amount of the blade member on the basis of the axial load; and correcting flexure of the blade member on the basis of the flexure amount calculated.

With thus controlling method, correction of flexure of the blade member can be properly performed on the basis of the flexure amount calculated from the axial load acting between the workpiece and the blade member.

A third aspect of the present invention provides a device for detecting a flexure of a blade member of a slicing machine in which a workpiece is placed in the blade member in the form of a flat ring and having an internal cutting edge on an internal periphery thereof, and a relative movement is rendered between the blade member being rotated and a workpiece in a radial direction of the blade member to produce a wafer of the workpiece, the detecting device comprising: load detecting means for detecting an axial load acting between the workpiece and the blade member; and flexure calculating means for calculating a flexure amount of the blade member on the basis of the axial load detected by the load detecting means.

Also, it is preferable that the flexure calculating means comprises: memory means for storing a reference axial load detected by the load detecting means before the workpiece is brought into contact with the blade member or a reference flexure amount corresponding to the reference axial load detected; and comparing means for comparing the reference axial load or reference flexure amount stored in the memory means with a latest axial load detected by the load detecting means after the workpiece is brought into contact with the blade member or a latest flexure amount corresponding to the latest axial load detected, thereby calculating an actual flexure amount on the basis of comparison result obtained by the comparing means.

A fourth aspect of the present invention provides a device for controlling the flexure of a blade member of a slicing machine in which a workpiece is placed in the blade member in the form of a flat ring and having an internal cutting edge on an internal periphery thereof, and a relative movement is rendered between the blade member being rotated and a workpiece in a radial direction of the blade member to produce a wafer of the workpiece, the controlling device comprising: load detecting means for detecting an axial load acting between the workpiece and the blade member; flexure calculating means for calculating a flexure amount of the blade member on the basis of the axial load detected by the load detecting means; and the flexure calculating means comprising correcting means for correcting the flexure amount on the basis of cutting force and inclination between an axial direction of the blade member and an axial direction of the workpiece.

A fifth aspect of the present invention provides a device for controlling the flexure of a blade member of a slicing machine in which a workpiece is placed in the blade member in the form of a flat ring and having an internal cutting edge on an internal periphery thereof, and a relative movement is rendered between the blade member being rotated and a workpiece in a radial direction of the blade member to produce a wafer of the workpiece, the controlling device comprising: load detecting means for detecting an axial load acting between the workpiece and the blade member; flexure calculating means for calculating a flexure amount of the blade member on the basis of the axial load detected by the load detecting means; the flexure calculating means comprises correcting means for correcting the flexure amount on the basis of weight of the workpiece and inclination between an axial direction of the blade member and an axial direction of the workpiece.

Furthermore, it is preferable that the load detecting means further detects a load acting in a direction normal to the axial load, and the correcting means of the flexure calculating means corrects the flexure amount on the basis of the load acting in the direction normal to the axial load.

A sixth aspect of the present invention provides a device for controlling the flexure of a blade member of a slicing machine in which a workpiece is placed in the blade member in the form of a flat ring and having an internal cutting edge on an internal periphery thereof, and a relative movement is rendered between the blade member being rotated and a workpiece in a radial direction of the blade member to produce a wafer of the workpiece, the controlling device comprising: flexure adjusting means for adjusting the flexure of the blade member; load detecting means for detecting an axial load acting between the workpiece and the blade member; flexure calculating means for calculating a flexure amount of the blade member on the basis of the axial load detected by the load detecting means; and control means for controlling the flexure adjusting means on the basis of the flexure amount calculated by the flexure calculating means.

The above and other objects, features and advantages of the present invention will become more apparent from the following detailed description which is to be read in conjunction with the accompanying drawings.

BRIEF DESCRIPTION OF THE DRAWINGS

FIGS. 9A and 9B illustrate dress directions for dress operation applied to the blade member;

DETAILED DESCRIPTION OF THE PREFERRED EMBODIMENTS

Figure 1:
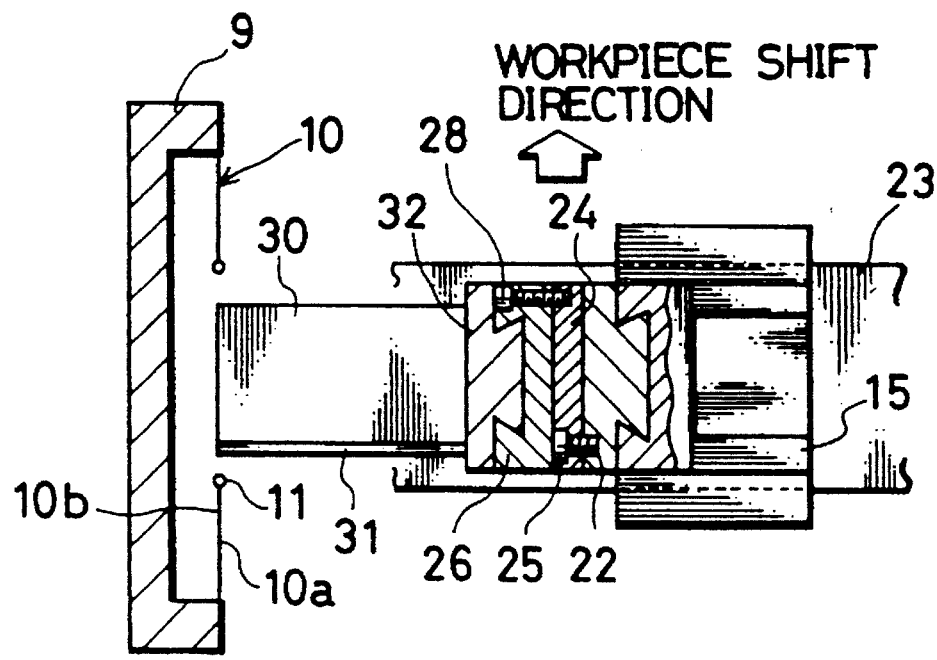
FIG. 1 is a partly sectional plane view showing an essential part of a slicing machine embodying the present invention.

Preferred embodiments of the present invention will be explained in detail with reference to accompanying drawings. First of all, it should be noted that in order to solve above problems, the inventors of this application studied hard and found the fact that the flexure amount is correlated with an axial load acting in the axial direction of the workpiece and the blade member in a proportional relationship as shown in a graph of FIG. 3. It is, therefore, found that the flexure condition can be known by detecting this axial load.

A first embodiment of the present invention will be explained with reference to FIGS. 1–10. A slicing machine, shown in FIGS. 4 and 5, comprises a base 1, on which parallel guide rails 2, 2 are provided. A slide table 3 is mounted on these guide rails 2, 2 to slide thereon.

A main spindle base 4 is provided on the base 1 at a position confronting with the slide table 3. This main spindle base 4 mounts a main bearing 4a thereon. The main bearing 4a supports one end of a main spindle 6 rotatably. The main spindle 6 is driven by a spindle drive motor 8 through a belt mechanism 7 entrained between one end of the main spindle 6 and an output shaft of the spindle drive motor 8. The other end of the main spindle 6 is connected to a rotary tension disk 9. This tension disk 9, driven by means of a rotational drive means 5 consisting of the main spindle 6, the belt mechanism 7, and the spindle drive motor 8, rotates about the main spindle 6.

The tension disk 9 has a circumferential periphery on which a flat, circular, ringed blade member 10 of doughnut shape is attached. This blade member 10 has an internal cutting edge 11 secured to an internal circumferential periphery thereof. The internal cutting edge 11 is made of diamond grain or the like material. When the tension disk 9 rotates, the rotational speed N varies. In accordance with change of the rotational speed N, the blade member 10 causes displacement in the axial direction of main spindle 6, i.e., in the rotational shaft direction of the blade member 10. Namely, when the tension disk 9 rotates, a centrifugal force acts on the circumferential periphery of the tension disk 9. Thus, the rotational speed N determines magnitude and direction of the displacement in the rotational shaft direction given from the tension disk 9 to the blade member 10.

The slide table 3 mounts a holding member 15 and a dividing feed means 18 thereon. The holding member 15 can slide on a guide rail 23 extending in the rotational direction of the blade member 10, and holds one end of a workpiece 30 made of silicon semiconductor ingot or the like material. The dividing feed means 18 includes a ball screw 16 and a holding member drive motor 17 for rotating this ball screw 16. By this dividing feed means 18, the holding member 15 is shifted in the axial direction of the main spindle 6 so that one end of the workpiece 30 slightly protrudes passing through a central hole of the blade member 10 from a front side 10a to a behind side 10b of the blade member 10.

The slide table 3 mounts a dress device 19 thereon. The dress device 19 is provided for dressing the internal cutting edge 11; therefore, the dress device 19 has a tool whose tip is disposed close to the internal cutting edge 11 of the blade member 10.

On the base 1, there is provided a cutting feed means 14, which comprises a ball screw 12 and a cutting feed motor 13 rotating this ball screw 12. By this cutting feed means 14, the slide table 3 can slide on the guide rails 2, 2 in the direction normal to the main spindle 6. Accordingly, by shifting this slide table 3 from this side of a sheet of FIG. 4 toward the remote side, the workpiece 30 causes mutual displacement with respect to the blade member 10 in a radial direction (i.e., the direction of an arrow A in FIG. 5). Thus, the workpiece 30 is disposed in the central hole of the blade member 10 and is then shifted against the rotating blade member 10 to slice a part of the workpiece 30 by the internal cutting edge 11 of the blade member 10 for production of a piece of wafer.

A slice base 31, made of carbon or the like material, is fixed on the workpiece 30 at a final cut portion where the internal cutting edge 11 finishes the cutting operation of the workpiece 30. Namely, this final cut position corresponds to an outer peripheral edge of the workpiece 30 downstream of the cutting feed direction. The fixation of the slice base 31 onto the workpiece 30 intends to prevent the cutting resistance acting on the blade member 10 from being suddenly released upon finish of the cutting operation of the workpiece 30. For the presence of this slice base 31, it becomes possible to prevent the final cut portion from being roughly cut or damaged.

Two flexure detecting sensors 20 and 21 are provided near the blade member 10 for detecting the flexure amount of the blade member 10. These flexure detecting sensors 20 and 21 are eddy current type (i.e., magnetic type), and are disposed at positions shown in FIGS. 5–7.

Namely, the flexure detecting sensors 20 and 21 are located out of the shifting zone C along which the workpiece 30 moves during the cutting feed operation, and are disposed at positions confronting with the front surface 10a of the blade member 10 (i.e., the right surface of the blade member 10 in FIGS. 4 and 6) In more detail, one flexure detecting sensor 20, referred to as an inlet sensor hereinafter, is disposed near an inlet position P1 of a workpiece cutting zone (P1–P2) corresponding to the shifting zone C. The other flexure detecting sensor 21, referred to as an outlet sensor hereinafter, is disposed near an outlet position P2 of the workpiece cutting zone (P1–P2). The inlet position P1 corresponds to an upstream end of the workpiece cutting zone (P1–P2) in the rotational direction B of the blade member 10, while the outlet position P2 corresponds to a downstream end thereof.

Furthermore, as a characteristic feature of this slicing machine, there is provided an arrangement for detecting an axial load acting between the workpiece 30 and the blade member 10 during slice operation of the workpiece 30. This detection of the axial load enables us to know magnitude and direction of flexure at the midway point of the blade member 10, i.e., at a position where contact between the blade member 10 and the workpiece 30 continues most longest. This arrangement will be explained in more detail with reference to FIGS. 1 and 2.

Figure 2:
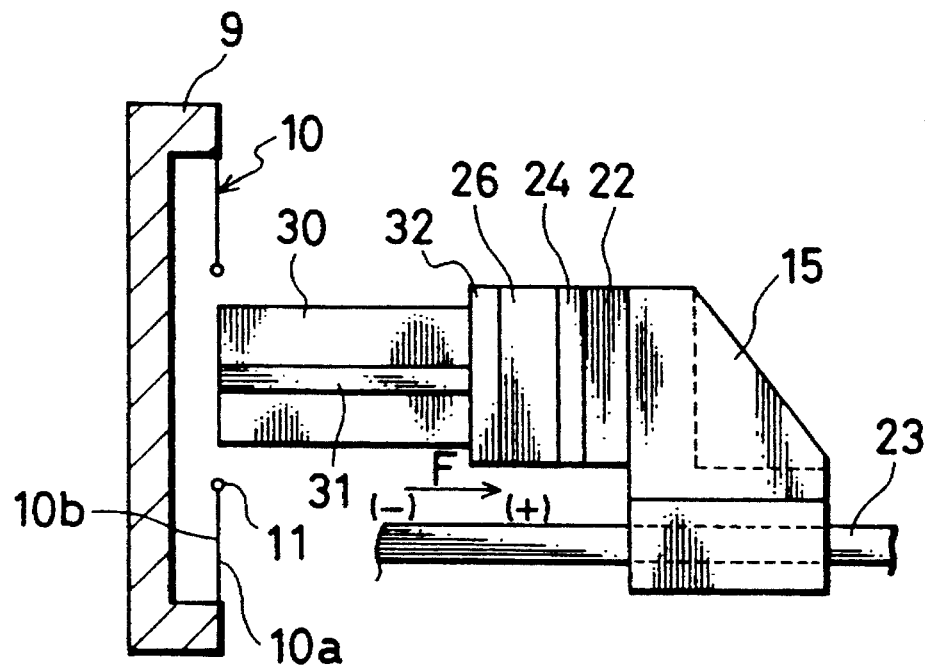
FIG. 2 is a partly sectional side view showing the essential part of the slicing machine.

The holding member 15 has one side surface, i.e., the left side surface in FIGS. 1 and 2, disposed closer to the workpiece 30, onto which a strain gage installation block 22 is detachably attached. A strain gage 24, i.e., a load detecting sensor, is secured onto the surface of the strain gage installation block 22 by means of a screw 25. Furthermore, a workpiece holding block 26 is secured onto the surface of the strain gage 24 by means of a screw 28.

The workpiece 30 has a base end surface (i.e., a right side surface in FIGS. 1 and 2) which is bonded to a workpiece installation block 32 by adhesive material. This workpiece installation block 32 is detachably coupled with the workpiece holding block 26. Namely, the strain gage 24 is interposed between the workpiece 30 and the holding member 15. The strain gage 24 receives a load acting on the workpiece during slicing operation and causes strain in proportion to this load; thus, the strain gage 24 generates an electric signal in accordance with the strain caused. In other words, an axial load acting between the blade member 10 and the workpiece 30 is converted into a measurement of the strain gage 24 and further converted into an electric signal.

Figure 6:
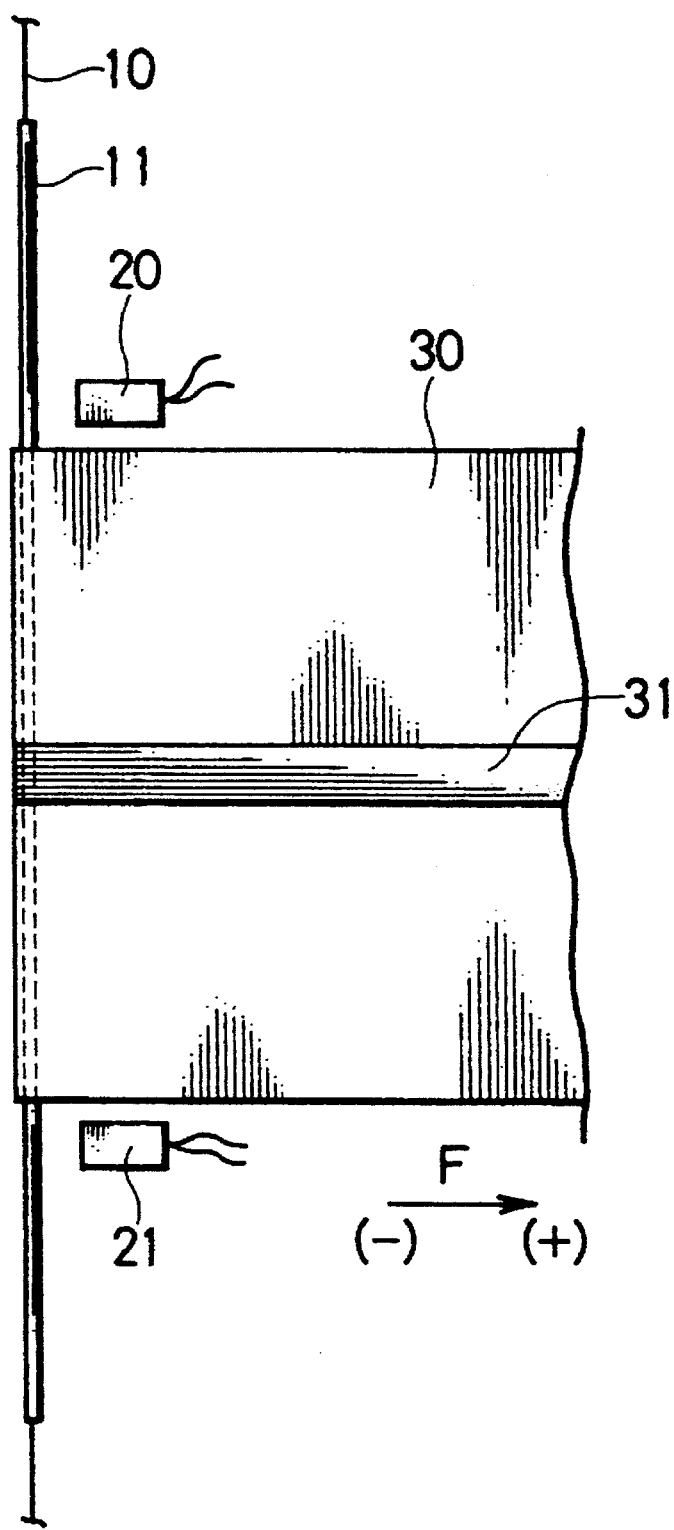
FIG. 6 is a side view enlargedly showing the blade member and the workpiece to be sliced.
Figure 7:
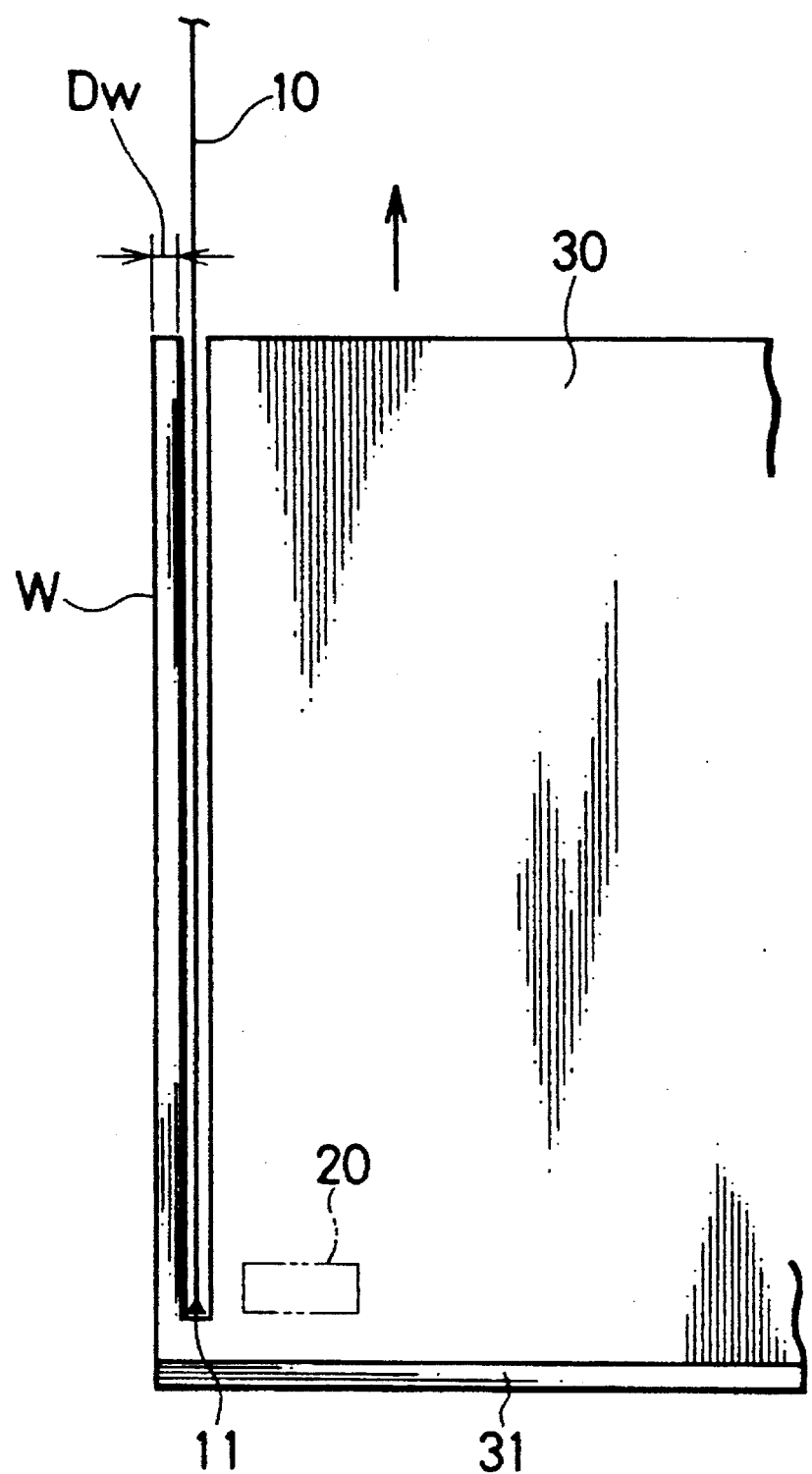
FIG. 7 is a plane view enlargedly showing the blade member and the workpiece to be sliced.

In this case, the strain gage 24 generates a positive signal when received a right-direction load (i.e., a compression load) as shown by an arrow F in FIGS. 2 and 6, and a negative signal when received a left-direction load (i.e., a tensile load).

In addition to these sensors, the above slicing machine includes a control unit 40 which will be explained in detail with reference to FIG. 8.

Figure 3:
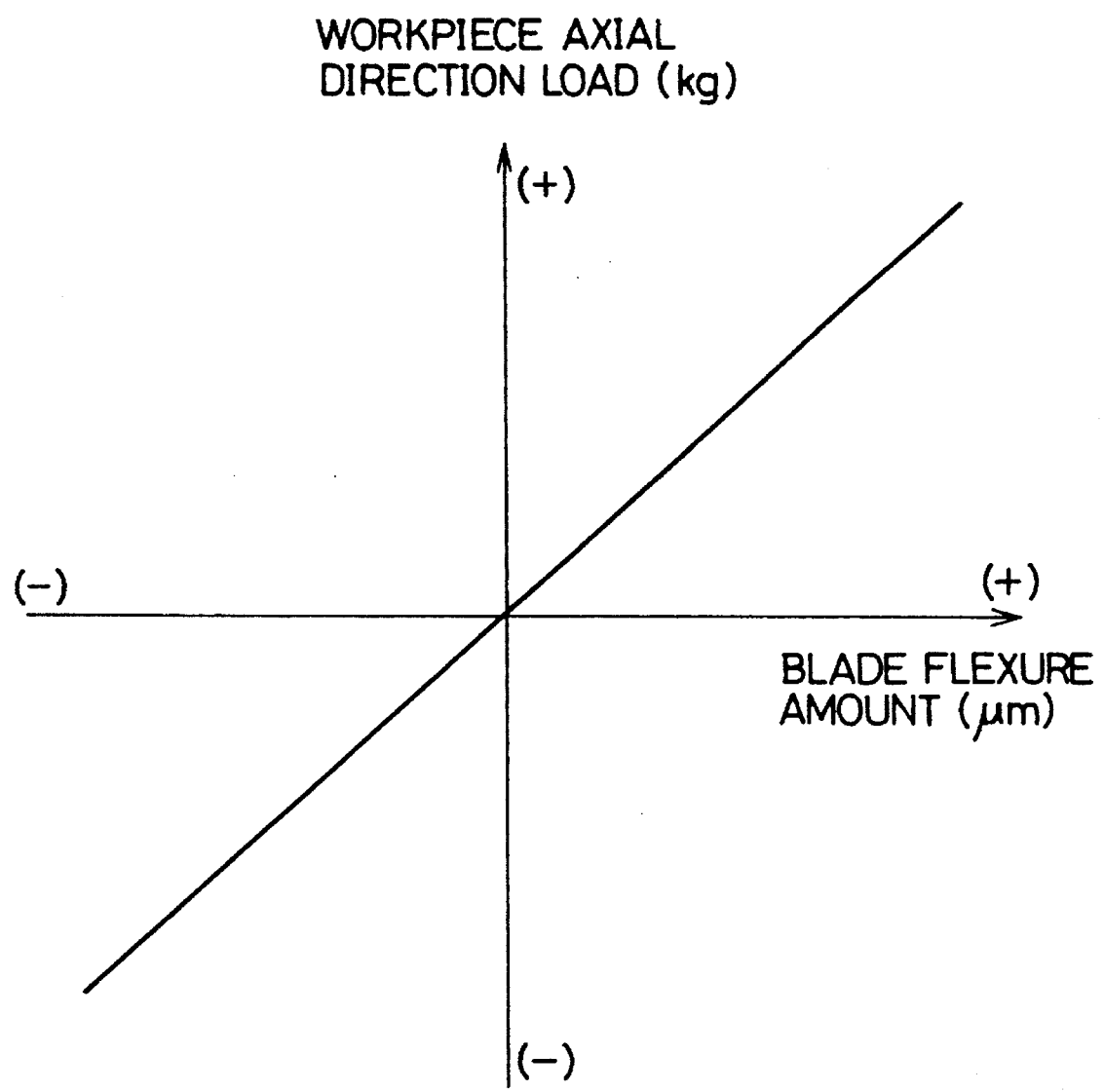
FIG. 3 is a graph showing a relationship between the flexure amount and an axial load acting in the axial direction of a workpiece and a blade member.
Figure 4:
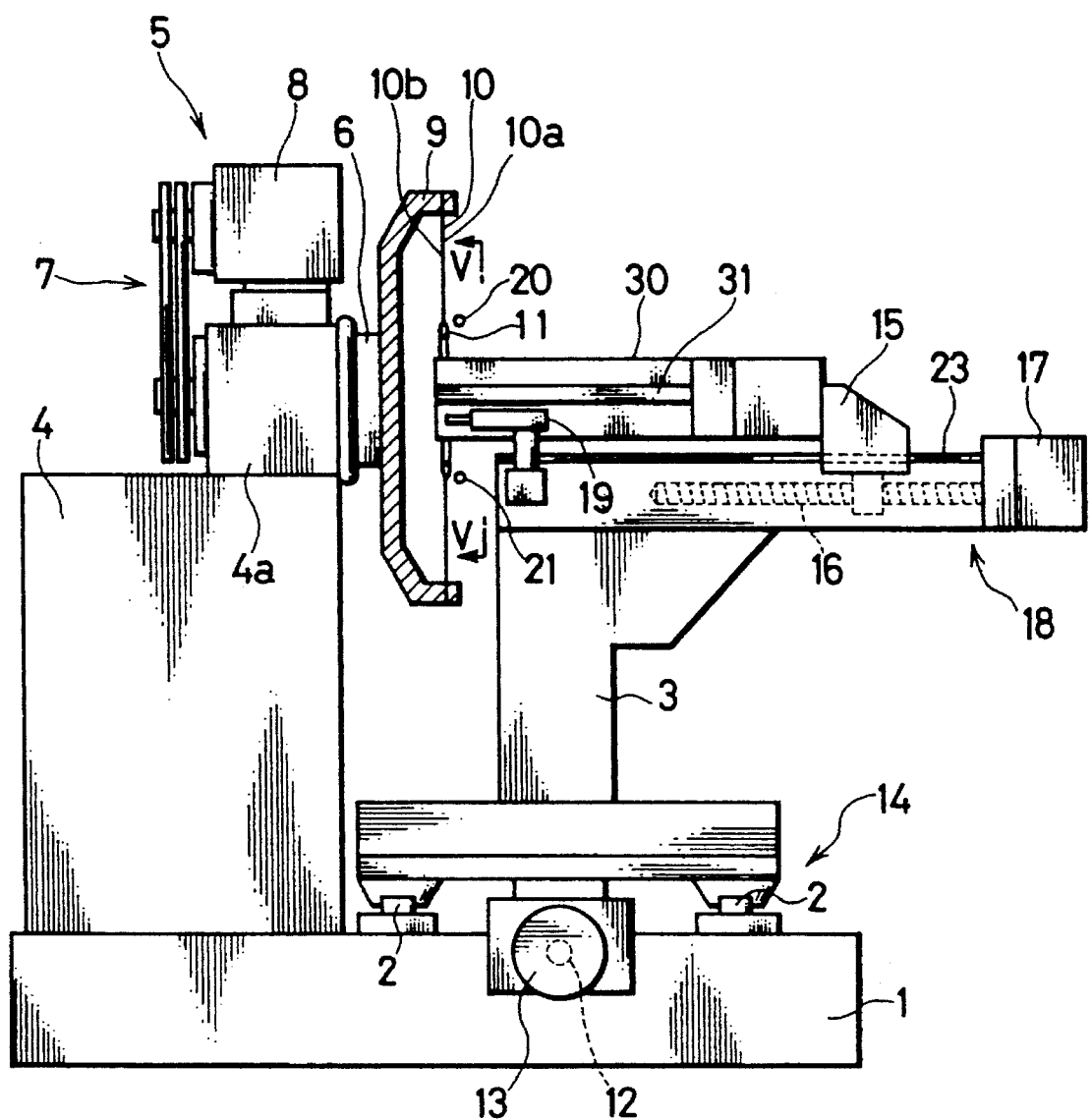
FIG. 4 is a partly sectional front view showing the slicing machine.
Figure 8:
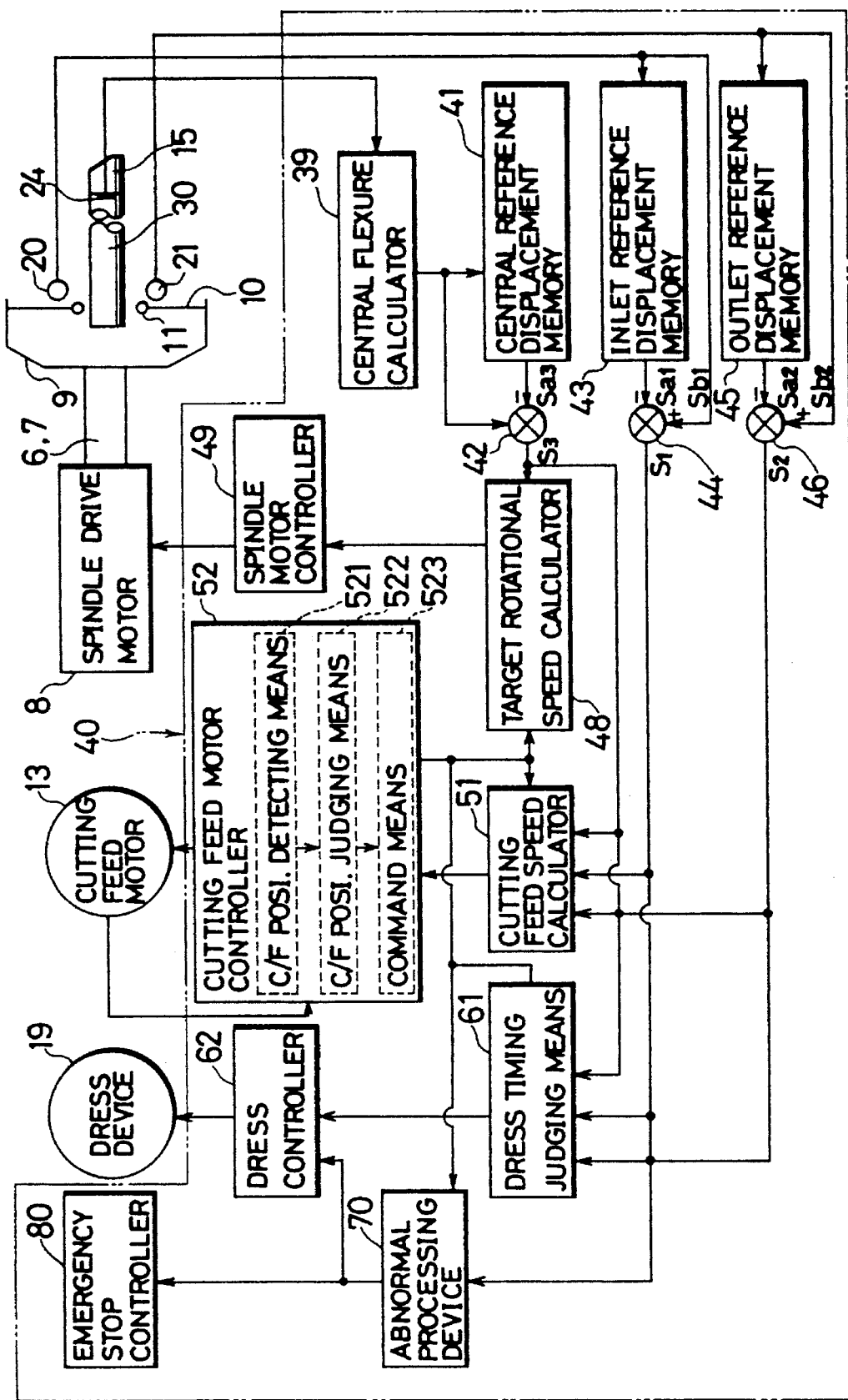
FIG. 8 is a block diagram showing functional constitution of a controller equipped in the slicing machine.

In FIG. 8, a central flexure calculator 39 calculates an axial flexure amount causing at a central portion of the blade member 10 on the basis of an output signal of the strain gage 24. In more detail, as explained above, the inventors of this application carried out experiments and found the fact that the axial load acting between the workpiece 30 and the blade member 10 is substantially proportional to the axial flexure amount at the central portion of the blade member 10 as shown in FIG. 3. As the strain gage 24 generates an electric signal corresponding to the axial load acting between the workpiece 30 and the blade member 10, the central flexure calculator 39 inputs the signal of the strain gage 24. Meanwhile, the central flexure calculator 39 stores a linear function representing the relationship of FIG. 3 to obtain direction and magnitude of the flexure corresponding to the axial load detected with reference to this linear function.

A central referential displacement memory (i.e., memory means) 41, an inlet referential displacement memory 43, and an outlet referential displacement memory 45 receive signals outputted from the central flexure calculator 39, the inlet sensor 20, and the outlet sensor 21, respectively. The central referential displacement memory 41 stores an output signal of the central flexure calculator 39 as a central referential flexure amount Sa3 when the workpiece 30 has just reached a reference position (slightly left of an alternating long and two short dashes line in FIG. 5) which is a position immediately before the slicing operation of the workpiece 30 begins. The central referential flexure amount Sa3 is not related to an actual flexure amount of the blade member 10 at all, which rather reflects an axial load acting on the workpiece 30 due to weight of the workpiece 30 before the blade member 10 is brought into contact with the workpiece 30. Hereinafter, this central referential flexure amount Sa3 is referred to as a provisional flexure amount.

The inlet referential displacement memory 43 stores an output signal of the inlet sensor 20 as an inlet referential flexure amount Sa1 when the workpiece 30 has just reached the reference position. In the same manner, the outlet referential displacement memory 45 stores an output signal of the outlet sensor 21 as an outlet referential flexure amount Sa2 when the workpiece 30 has just reached the reference position. By the way, a cutting feed position detecting means 521 of a cutting feed motor controller 52 later described is utilized to make a judgment as to whether or not the workpiece 30 has reached the reference position.

Above referential flexure amounts Sa3, Sa1, and Sa2 stored in the corresponding memories 41, 43, and 45 are subsequently fed to a central displacement comparator (i.e., comparing means) 42, an inlet displacement comparator 44, and an outlet displacement comparator 46, respectively. The central displacement comparator 42 inputs a latest central flexure amount Sb3 calculated by the central flexure calculator 39 in addition to the above central referential flexure amount Sa3, and then, obtains an actual central flexure amount S3 at the midway point P3 of the blade member 10 by subtracting the central referential flexure amount Sa3 from the latest central flexure amount Sb3. Namely, the central displacement comparator 42, the central flexure calculator 39, and the central referential displacement memory 41 constitute a flexure calculating means for calculating an actual flexure amount of the blade member on the basis of the detecting signal outputted from the strain gage 24.

Similarly, the inlet displacement comparator 44 inputs a latest inlet flexure amount Sb1 detected by the inlet sensor 20 in addition to the above inlet referential flexure amount Sa1, and then, obtains an actual inlet flexure amount S1 at the inlet portion P1 of the blade member 10 by subtracting the inlet referential flexure amount Sa1 from the latest inlet flexure amount Sb1. The outlet displacement comparator 46 inputs a latest outlet flexure amount Sb2 detected by the outlet sensor 21 in addition to the above outlet referential flexure amount Sa2, and then, obtains an actual outlet flexure amount S2 at the outlet portion P2 of the blade member 10 by subtracting the outlet referential flexure amount Sa2 from the latest inlet flexure amount Sb2.

The actual flexure amounts S1, S2, S3 calculated in the displacement comparators 42, 44, and 46 are inputted into a cutting feed speed calculator 51 and a dress timing judging means 61. The actual central flexure amount S3 is further inputted into a target rotational speed calculator (i.e flexure control means) 48.

The target rotational speed calculator 48 calculates a target rotational speed Na of the tension disk 9 required for decreasing the actual central flexure amount S3 to 0 on the basis of the actual central flexure amount S3 detected by the central displacement comparator 42 and the actual rotational speed of the tension disk 9 in response to a drive command signal fed from a command means 523 of the cutting feed motor controller 52. A signal corresponding to this target rotational speed Na is fed to a spindle motor controller (i.e., flexure adjusting means) 49. The spindle motor controller 49 controls the spindle drive motor 8 in such a manner that the rotational speed of the tension disk 9 is equalized to the above target rotational speed Na when received the signal from the target rotational speed calculator 48 and to a predetermined fundamental rotational speed N0 when received no signal form the target rotational speed calculator 48.

The cutting feed speed calculator 51, when received the drive signal from the command means 523 of the cutting feed motor controller 52, calculates a target cutting feed speed Va on the basis of the actual flexure amounts S1, S2, and S3 detected by the displacement comparators 44, 46, and 42, respectively. This target cutting feed speed Va is used for reducing the actual central flexure amount S3, a difference $\Delta S1$ between the inlet flexure amount S1 and the central flexure amount S3, and a difference $\Delta S2$ between the outlet flexure amount S2 and the central flexure amount S3. A signal corresponding to the target cutting feed speed Va is fed to the cutting feed motor controller 52. Calculation of the target cutting feed speed Va is, for example, carried out based on an equation $Va=V0-kS$, where V0 is a predetermined fundamental cutting feed speed, k is a coefficient, and S is the largest value among the absolute values of the S3, $\Delta S1$, and $\Delta S2$.

The cutting feed speed calculator 51 makes a judgment based on the above value S as to whether or not a predetermined cutting feed speed calculating condition is satisfied. If the cutting feed speed calculating condition is not satisfied, i.e if the above value S is not larger than a predetermined value, the calculation of the target cutting feed speed Va is suspended and, therefore, no signal is outputted to the cutting feed motor controller 52.

The cutting feed motor controller 52 controls the cutting feed motor 13 in such a manner that the cutting feed speed V is equalized to the target cutting feed speed Va obtained in the cutting feed speed calculator 51 when received a signal from the cutting feed speed calculator 51 and to the fundamental cutting feed speed V0 when received no signal from the cutting feed speed calculator 51. In more detail, the cutting feed motor controller 52 comprises a cutting feed position detecting means 521, a cutting feed position judging means 522, and the command means 523.

The cutting feed position detecting means 521 detects a cutting feed position (i.e., a position in the cutting feed direction) of the workpiece 30 on the basis of a pulse signal detected from the cutting feed motor 13. The cutting feed position judging means 522 makes a judgment based on the above cutting feed position detected by the cutting feed position detecting means 521 as to whether or not the cutting feed position of the workpiece 30 is in a zone L. This zone L ranges from a cutting initiating position (the position indicated by the alternate long and two short dashes line left in FIG. 5) to a cutting terminating position (a position indicated by an alternate long and two short dashes line right in FIG. 5). The cutting terminating position is a position where the slice base 31 just arrives the internal cutting edge 11 of the blade member 10. The command means 523 supplies the target rotational speed calculator 48, the cutting feed speed calculator 51, and the dress timing judging means 61 with a drive command signal when the cutting feed position of the workpiece 30 is in the zone L and a stop command signal when the cutting feed position of the workpiece 30 is out of the zone L.

The dress timing judging means 61, when received the drive command signal from the command means 523, makes a judgment based on the value S whether or not a dress operation by the dress device 19 is required. If the dress operation is required, the dress timing judging means 61 outputs a command signal to a dress controller 62 so as to activate the dress device 19 at an appropriate timing. Details of control will be described later.

Furthermore, the control unit 40 performs control of the holding member drive motor 17 which feeds the workpiece 30 with respect to the blade member 10 for dividing. A reference numeral 70 represents an abnormal processing device for detecting abnormal condition. A reference numeral 80 represents an emergency stop controller.

Figure 10A:
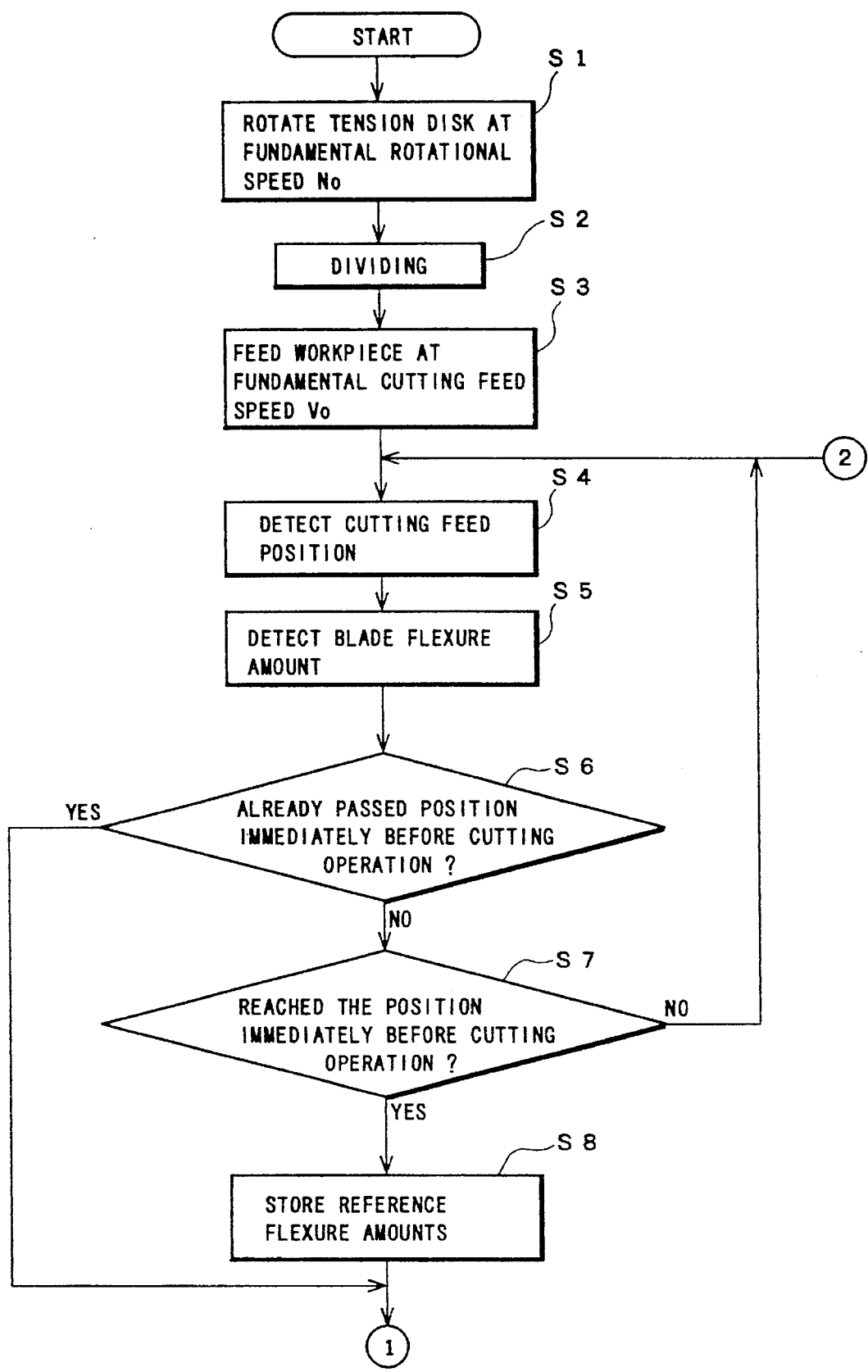
FIGS. 10A to 10C are flowcharts combinedly showing a control operation carried out in the slicing machine.
Figure 10B:
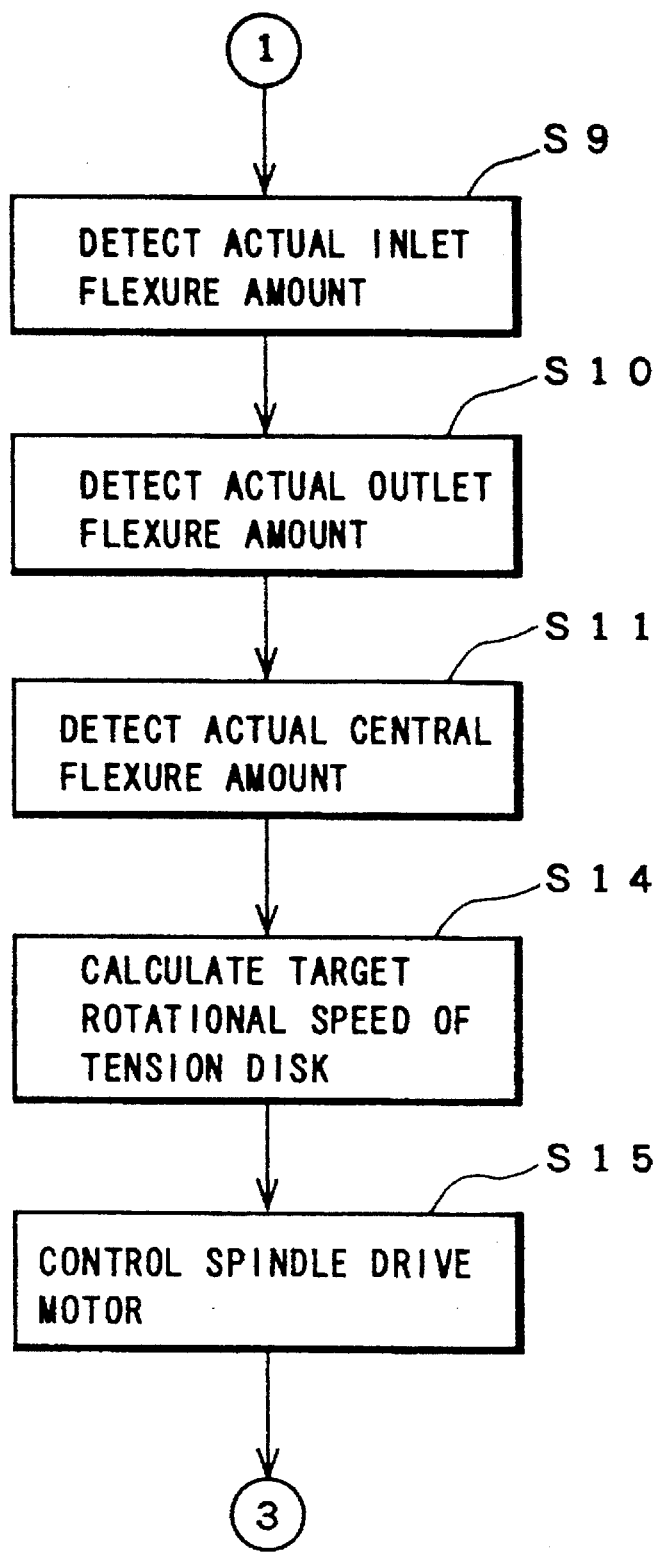
Figure 10C:
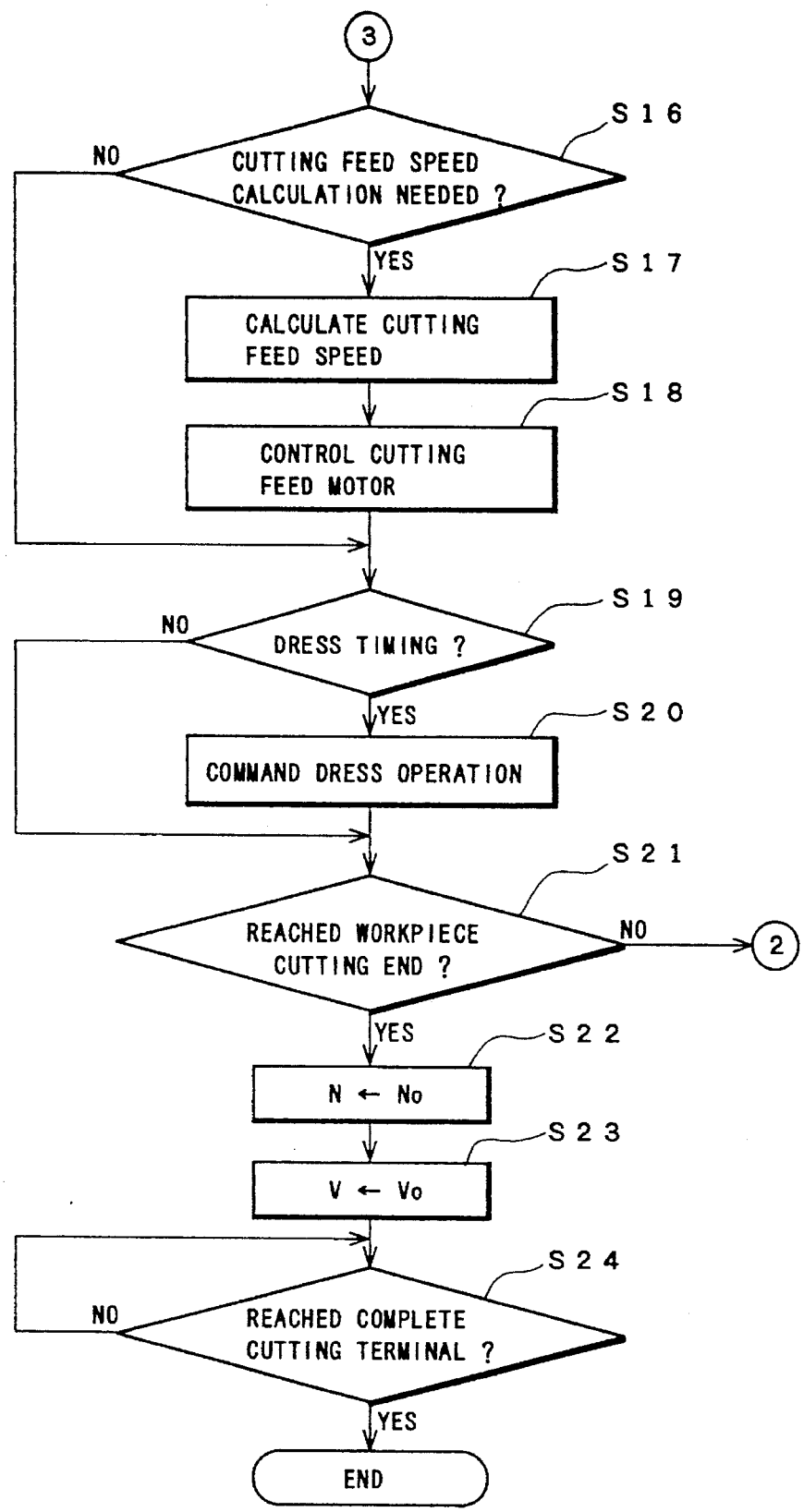

Next, control of the control unit 40 and operation of the slicing machine in accordance with the control of the control unit 40 will be explained with reference to the flowcharts of FIGS. 10A to 10C.

First of all, in Step S1, the control unit 40 controls the rotational drive means 5 to rotate the tension disk 9 at the fundamental rotational speed N0. In Step S2, the control unit 40 controls the dividing feed means 18 to shift the workpiece 30 held by the holding member 15 toward the main spindle 6. With this slide movement, one end of the workpiece 30 protrudes slightly passing through the central hole of the blade member 10 from the front side 10a to the behind side 10b of the blade member 10.

Next, in Step S3, the cutting feed means 14 shifts the workpiece 30 at the fundamental cutting feed speed V0 in the radial direction of the blade member 10. In Step S4, the cutting feed position detecting means 521 detects a cutting feed position of the workpiece 30. Then in Step S5, the inlet and outlet flexure detecting sensors 20 and 21 detect latest inlet and outlet flexure amounts Sb1 and Sb2, respectively, and the central flexure calculator 39 calculates a flexure amount (i.e., a provisional flexure amount) corresponding to the detecting signal of the strain gage 24 with reference to the graph of FIG. 3.

Figure 5:
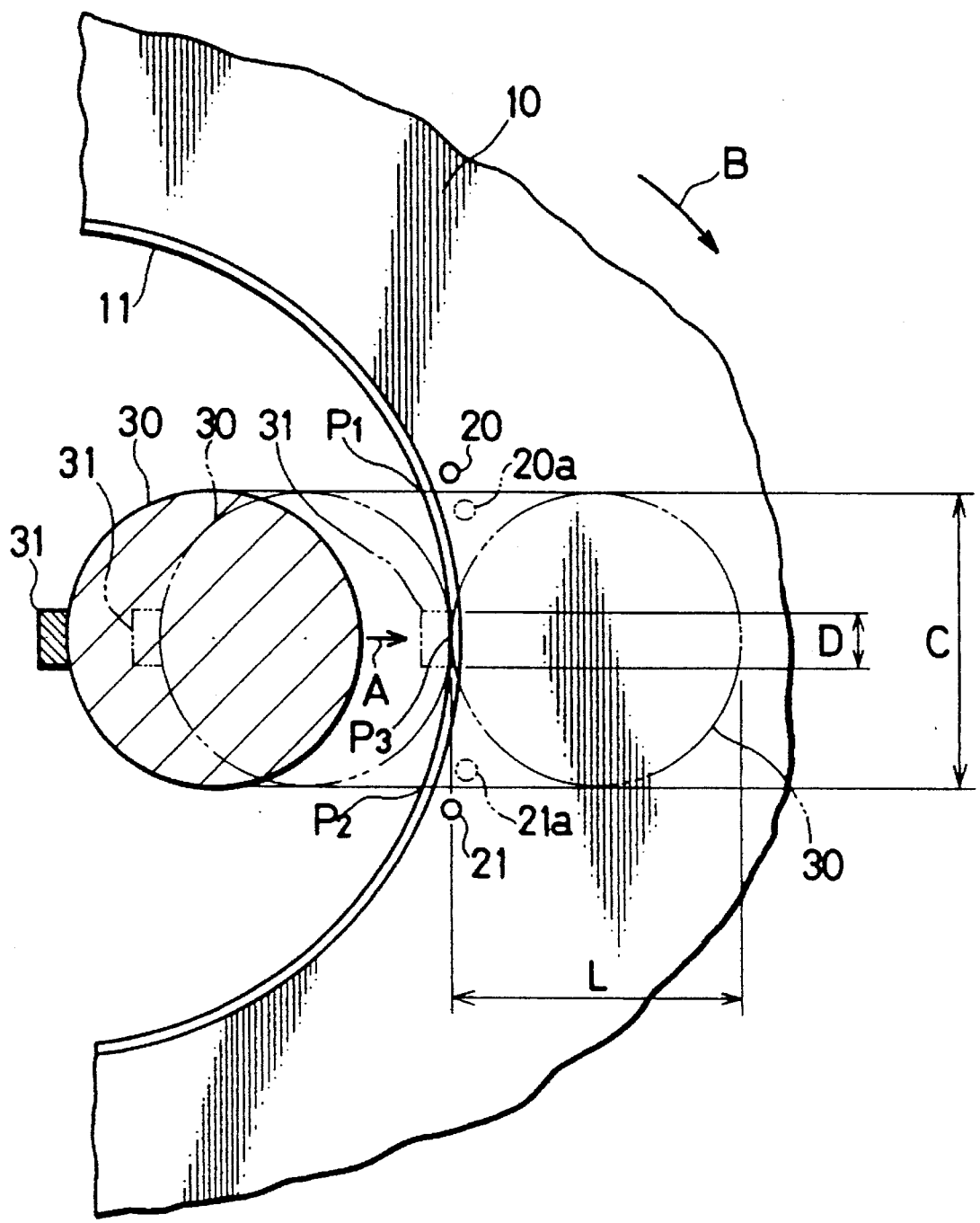
FIG. 5 is a sectional view taken along the line V—V of FIG. 4.

Subsequently, in consecutive two Steps S6 and S7, the cutting feed position judging means 522 makes a judgment as to whether or not the workpiece 30 has already reached the reference position which is the position immediately before initiating cutting operation shown in FIG. 5. If the workpiece 30 arrives the reference position for the first time, i.e., if the judgment of Step S6 is NO and the judgment of Step S7 is YES, the latest flexure amounts Sb1, Sb2, and Sb3 are stored as the referential flexure amounts Sa1, Sa2, and Sa3 in Step S8. If the judgment of Step S7 is NO, the control unit 40 returns to Step S4.

Once these referential flexure amounts Sa1, Sa2, and Sa3 are stored, Steps S9 to S11 calculate the actual flexure amount S1, S2, and S3 on the basis of these referential flexure amounts Sa1, Sa2, and Sa3. Since the judgment of Step S6 is always YES after the workpiece 30 has once reached the reference position, no storing of flexure amounts is newly performed in Step S8.

Next, in Step S14, the target rotational speed calculator 48 calculates the target rotational speed Na of the tension disk 9 on the basis of the central flexure amount S3. Thereafter, in Step S15, the spindle drive motor 8 is controlled to equalize the actual rotational speed N of the tension disk 9 to the target rotational speed Na. With this operation, the blade member 10 causes a displacement in the direction where the flexure amount reduces in the vicinity of the midway point P3 of the blade member 10, thereby adjusting an overall flexure amount of the blade member 10. In response to this adjusting operation, the cutting feed speed calculator 51 makes a judgment in Step S16 as to whether or not the cutting feed speed calculation is needed, i.e., whether or not any of the absolute values of S3, $\Delta$S1, and $\Delta$S2 exceeds a predetermined allowable limit R1. If the cutting feed speed calculation condition is satisfied, the control unit 40 proceeds to Step S17 to cause the cutting feed speed calculator 51 to obtain the target cutting feed speed Va on the basis of the flexure amounts S1, S2, and S3. Subsequently, the control unit 40 proceeds to Step S18 to drive the cutting feed motor 13 so that the cutting feed speed V is equalized to the target cutting feed speed Va. With this operation the cutting feed speed V decreases to approach the target cutting feed speed Va; therefore, cutting resistance decreases correspondingly. This reduction of cutting resistance allows the blade member 10 to reduce its axial flexure, i.e., the flexure amounts $\Delta$S1 and $\Delta$S2, due to elastic restoring force. By the way, no adjustment is performed when the judgment of Step S16 is NO since the control unit 40 skips Steps S17 and S18.

Subsequently, in Step S19, the dress timing judging means 61 makes a judgment based on the value S as to whether or not the predetermined dress condition is satisfied. The dress condition is fulfilled when the absolute value of S3 exceeds a predetermined critical value R2 (>R1), the absolute value of $\Delta$S1 exceeds a predetermined critical value R3 (>R1), or the absolute value of $\Delta$S2 exceeds a predetermined critical value R3 (>R1). If the dress condition is satisfied in Step S19, the control unit 40 proceeds to Step S20 to cause the dress controller 62 to output a dress command signal. In response to this dress command signal, the dress device 19 performs the dress operation after the cutting operation of the workpiece 30 is finished. A dress direction shown in FIG. 9A is set when the axial load F detected by the strain gage 24 is positive, and a dress direction shown in FIG. 9B is set when the axial load F is negative.

Next, in Step S21, the control unit 40 makes a judgment as to whether or not the cutting operation of the workpiece 30 is terminated. If the workpiece 30 has reached the cutting terminating position shown in FIG. 5, the control unit 40 proceeds to Step S22 to switch the rotational speed N of the tension disk 9 to the fundamental rotational speed N0 and, further, to Step S23 to switch the cutting feed speed V to the fundamental cutting feed speed V0. If the workpiece 30 has not reached the cutting terminating position, the control unit 40 returns to Step S4.

Next, the control unit 40 makes a judgment in Step S24 as to whether or not the workpiece 30 further advances until it reaches a complete cutting terminal where the slice base 31, as well as the workpiece 30, is completely cut. If the workpiece 30 has reached the complete cutting terminal, the control operation is ended.

As described above, in accordance with the slicing machine of the present invention, the axial load acting between the blade member 10 and the workpiece 30 during slicing operation is detected by the strain gage 24. The flexure amount of the blade member 10 is calculated based on the axial load detected. Accordingly, it is not necessary to use an eddy current sensor having been conventionally provided at a position confronting with the front end surface of the workpiece 30. In other words, a wafer machined gives no affection to the flexure amount detected through the strain gage 24. Thus accurate flexure detection is ensured. Furthermore, the present invention enables us to detect a flexure amount of a central (or midway) portion of the blade member 10 accurately and easily. Therefore, correction control of the flexure amount, i.e., blade rotational speed control in this embodiment, is properly carried out.

Moreover, in accordance with the present invention, a provisional flexure amount is detected. Namely, an axial load is detected before the blade member 10 is brought into contact with the workpiece 30. If an axial load acting on the workpiece 30 in a free condition is obtained, a provisional flexure amount corresponding to this axial load is obtained with reference to the graph of FIG. 3. This provisional flexure amount is used to obtain an actual flexure amount by comparing a detected flexure amount with this provisional flexure amount after the blade member 10 is brought into contact with the workpiece 30. Namely, by detecting the provisional flexure amount, noise components such as an axial load due to weight of the workpiece 30 can be removed and an accurate flexure amount detection is ensured.

Although the above embodiment compares the flexure amounts calculated on the basis of the axial loads detected by the strain gage 24 before and after the workpiece 30 is brought into contact with the blade member 10, it is also desirable to directly compare the axial loads themselves and then calculate a flexure amount based on the difference between the axial loads.

Figure 12:
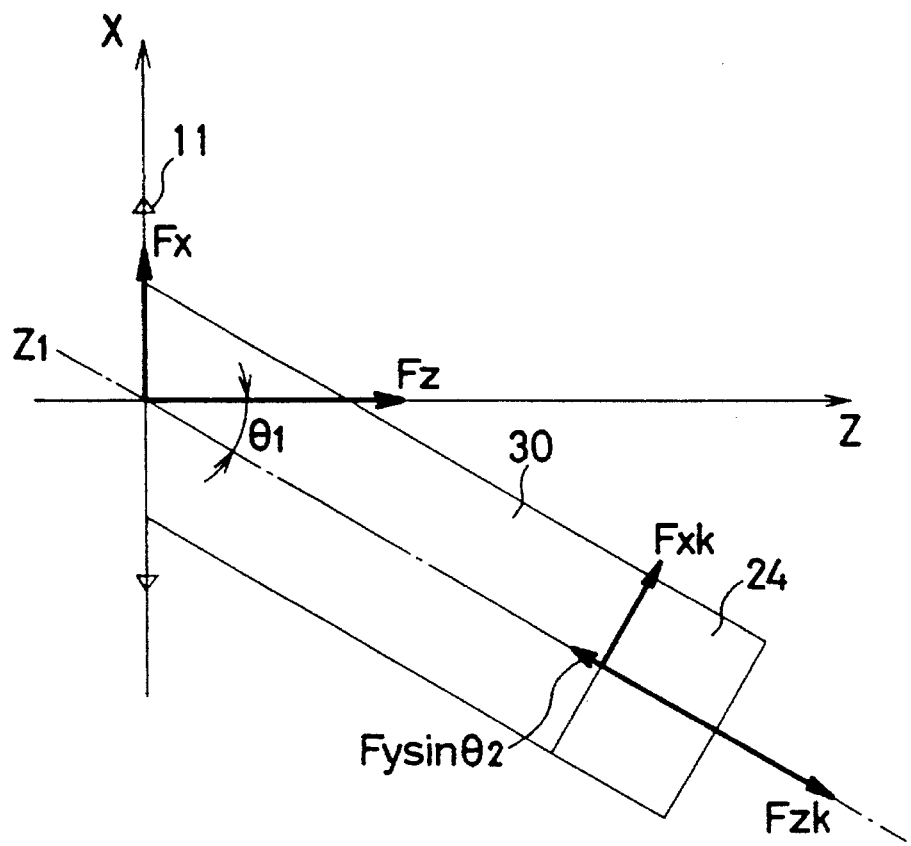
FIG. 12 is a plane view illustrating relationship between a load detected by the strain gage and the blade axial load.
Figure 13:
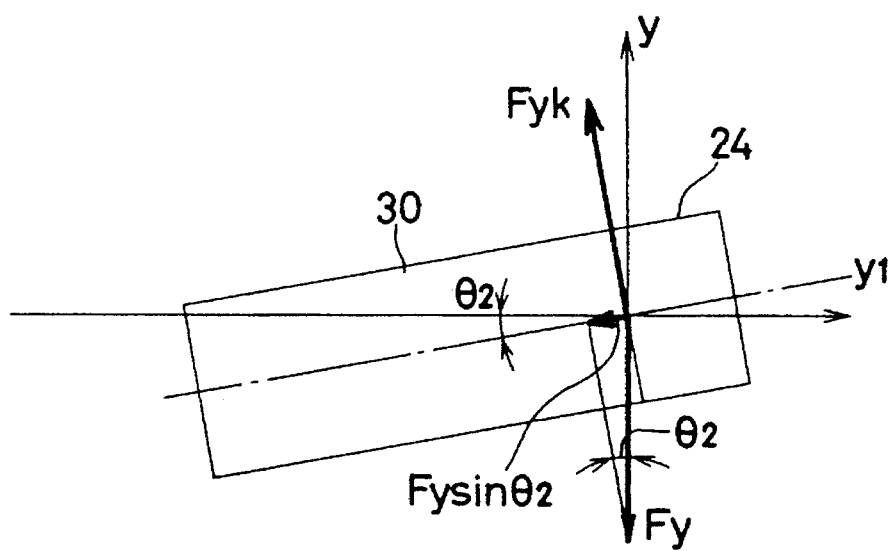
FIG. 13 is a side view illustrating relationship between the load detected by the strain gage and the blade axial load.
Figure 14:
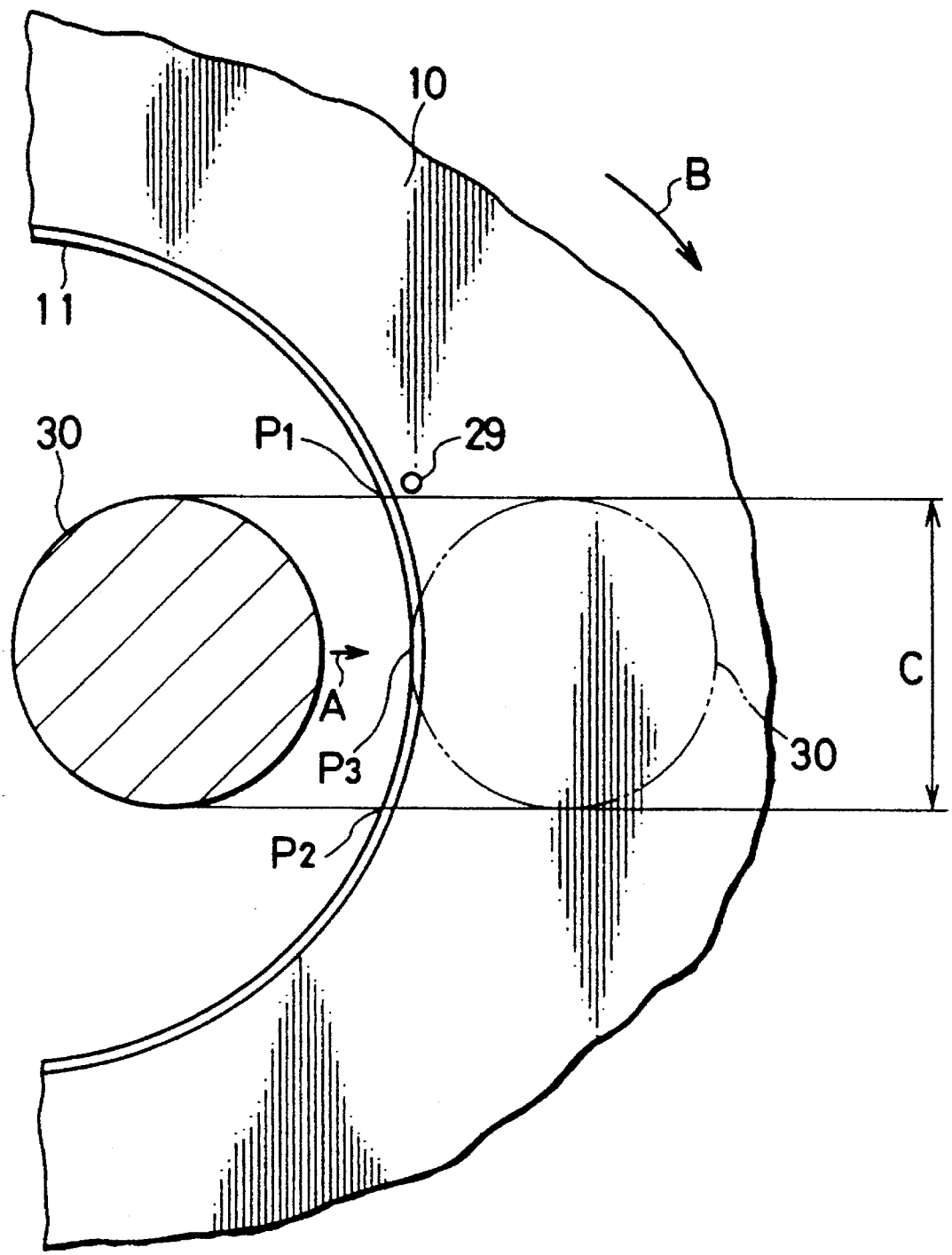
FIG. 14 is a partial sectional plane view showing one example of a conventional slicing machine.

Hereinafter, a second embodiment of the present invention will be explained with reference to FIGS. 11–13.

Although the axial direction of the workpiece 30 and the axial direction of the blade member 10 coincide with each other in the above first embodiment, the axial direction of the workpiece 30 may need to be inclined with respect to the axial direction of the blade member 10 because crystal direction of the workpiece 30 made of ingot is not always constant. In such a case, detecting only the axial load acting on the workpiece 30 as disclosed in the first embodiment cannot ensure accurate detection of the blade flexure because correction due to inclination is normally required.

In the second embodiment, it is supposed that the axial direction (i.e., a line z1 in FIG. 12) of the workpiece 30 is inclined with respect to the axial direction (i.e., the z-axis in FIG. 12) of the blade member 10 by an angle $\theta_1$. Furthermore, the axial direction (i.e., a line y1 in FIG. 13) of the workpiece 30 is inclined in an up-and-down direction by an angle $\theta_2$.

The second embodiment of the present invention is structurally identical with the first embodiment except for the strain gage 24. The strain gage 24 used in the second embodiment is a three-dimensional strain gage shown in FIG. 11, which is capable of detecting an axial load Fzk acting in the axial direction of the workpiece 30, a horizontal load Fxk, and a vertical load Fyk respectively acting in a direction normal to the axial direction of the workpiece 30. This strain gage 24 comprises a base 24A on which a plurality of (e.g., 4) piezoelectric sensors 24C, - - - , 24C are mounted, and a top plate 24B mounted on the base 24A so as to cover respective piezoelectric sensors 24C, - - - , 24C. The base 24A is secured on the strain gage installation block 22 by means of the screw 25 shown in the first embodiment. The top plate 24B is secured on the workpiece holding block 26 by means of the screw 28 shown in the first embodiment.

Figure 11:
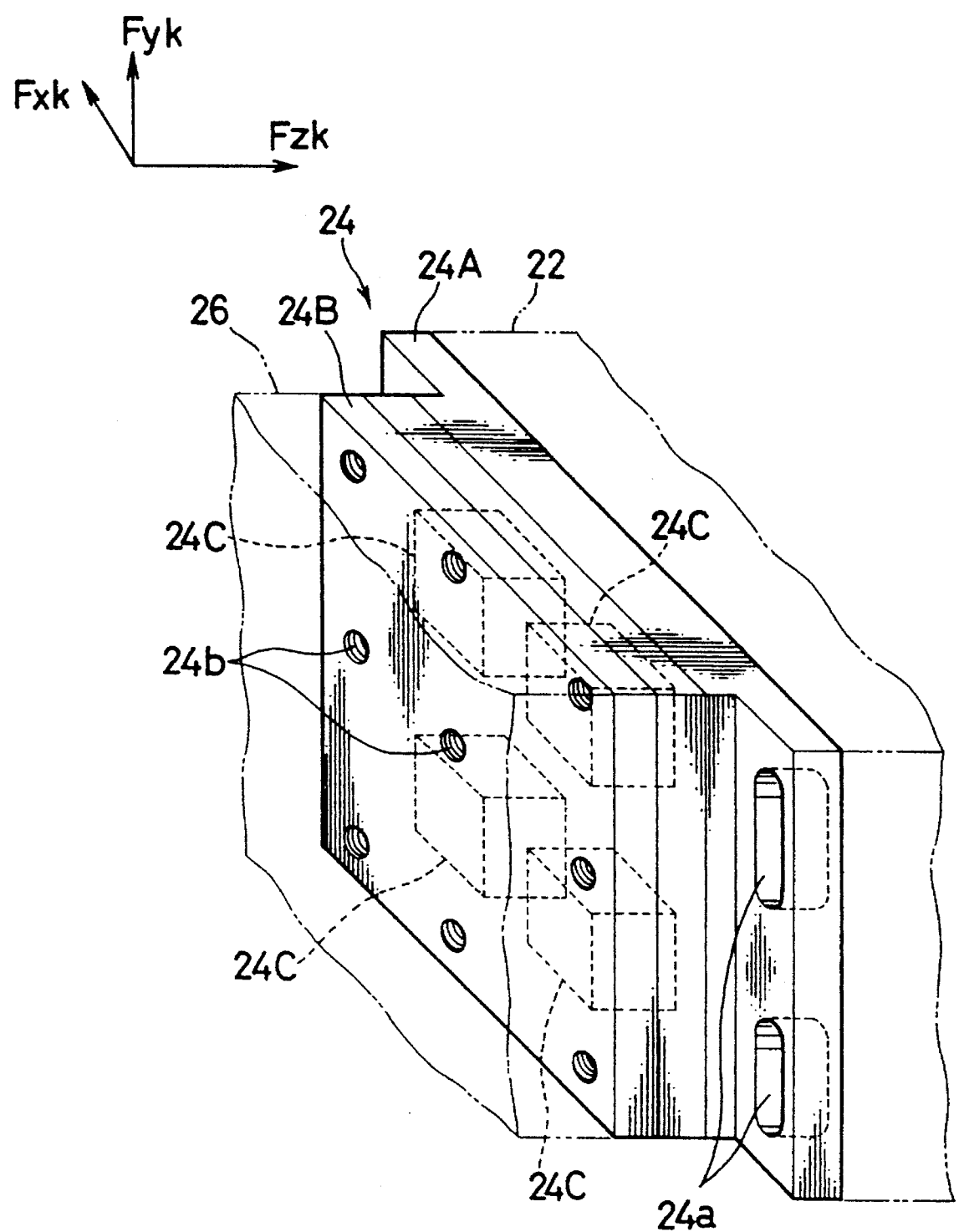
FIG. 11 is a perspective view showing a strain gage.

In FIG. 11, a reference numeral 24a denotes an insertion hole for the screw 25 and a reference numeral 24b denotes an insertion hole for fixing the top plate 24B to the base 24A.

The strain gage 24 detects three-dimensional loads Fxk, Fyk, and Fzk on the basis of the deformation amounts detected by respective piezoelectric sensors 24C, - - - , 24C. Three-dimensional loads Fxk, Fyk, and Fzk are supplied to the central flexure calculator 39. It is noted that conventionally known three-dimensional displacement sensors will be used for the strain gage 24 in this second embodiment.

The central flexure calculator 39 calculates an axial lead Fz of the blade member 10 on the basis of the three-dimensional loads Fxk, Fyk, and Fzk to obtain a central flexure amount.

A principle for this calculation will be explained below. If the blade member 10 has no flexure in the Z-axis direction and the workpiece 30 lies on the z1 line without inclining with respect to the y axis, the axial load of the workpiece 30 is expressed by the following equation.

$$Fzk = Fx \sin \theta_1 \tag{1}$$

Where, Fx represents an x-axis lead due to cutting force given to the workpiece 30 by the blade member 10, and Fy represents a y-axis load due to weight of the workpiece 30.

If the z-axis load Fz generated by the cutting force of the blade member 10 and the workpiece weight Fy are added, the axial load of the workpiece 30 is expressed by the following equation.

$$\begin{aligned} Fzk &= fx \sin \theta_1 + Fy \sin \theta_2 + Fz \cos \theta_1 \\ &\approx Fx \sin \theta_1 + Fy \sin \theta_2 + Fz \\ &(\because \cos \theta_1 \approx 1) \end{aligned} \tag{2}$$

Accordingly, the following equation is obtained.

$$Fz \approx Fzk - Fx \sin \theta_1 - Fy \sin \theta_2 \tag{3}$$

Furthermore, the following equations are obtained with respect to the loads Fxk and Fyk.

$$Fxk = Fx \cos \theta_1 + Fz \sin \theta_1 \approx Fx + Fz \sin \theta_1 \tag{4}$$

$$Fyk = Fy \cos \theta_2 \approx Fy \ (\because \cos \theta_2 \approx 1) \tag{5}$$

Modifying above four equations and recognizing $\sin^2 \theta_1 \approx 0$ obtains the following equation which is similar to the equation (3).

$$Fz = Fzk - Fxk \sin \theta1 - Fyk \sin \theta2 \qquad (5)$$

In accordance with the above equations, the flexure amount can be accurately calculated on the basis of the loads detected by the three dimensional displacement sensor.

By the way, the right hand third term (−Fyk sin θ2) of the equation (5) can be omitted if the axial size and weight of the workpiece 30 are relatively small. Namely, when the y-axis load Fy is sufficiently small or the detection value of the strain gage 24 is reset after setting the workpiece 30, omission of the right hand third term (−Fyk sin θ2) becomes possible.

Furthermore, if the cutting force Fx is detected from cutting power (i.e., electric power increase of the cutting feed motor 13 in the beginning of the cutting operation), this cutting force Fx is directly substituted in the equation (1) without detecting the load Fxk by the strain gage 24.

The present invention is not limited to the above embodiments. For example, the following aspects will be employed.

(1) The inlet and outlet sensors 20 and 21 used in the above embodiments can be omitted since the strain gage 24 alone can detect the flexure of the blade member 10 and allow to adjust the flexure amount.

(2) The axial load acting between the blade member 10 and the workpiece 30 can be detected by providing the strain gage 24 at the blade member side. For example, an axial load acting on the main spindle 6, to which the tension disk 9 supporting the blade member 10 is connected, can be detected.

(3) The blade member 10 can be shifted in its radial direction with respect to the stationary workpiece 30.

(4) The load Fxk is used for controlling the cutting force.

As this invention may be embodied in several forms without departing from the spirit of essential characteristics thereof, the present embodiments are therefore illustrative and not restrictive, since the scope of the invention is defined by the appending claims rather than by the description preceding them, and all changes that fall within meets and bounds of the claims, or equivalence of such meets and bounds are therefore intended to embraced by the claims.

What is claimed is:

1. A method for detecting the flexure of a blade member of a slicing machine in which a workpiece is placed in the blade member and in which the blade member is in the form of a flat ring, said workpiece having a forward longitudinal end and a rear longitudinal end, said blade member having an internal cutting edge on an internal periphery of the blade member, and wherein the blade member is rotated and relative movement is rendered between the rotated blade member and the workpiece in a radial direction of the blade member to produce a wafer from the forward longitudinal end of the workpiece, the detecting method comprising the steps of:

disposing an axial load detecting means at said rear longitudinal end of said workpiece with said axial load detecting means being generally axially aligned with said workpiece;

detecting the axial load acting between the workpiece and the blade member; and calculating the flexure amount of the blade member on the basis of the axial load.

2. A method according to claim 1 wherein said workpiece has a cylindrical configuration said step of rendering relative movement between the blade member and the workpiece comprising moving the workpiece in a radial direction to produce a wafer, said workpiece in moving in said radial direction traversing a swath path defined by two parallel planes spaced from one another a distance corresponding to the diameter of said cylindrical workpiece, a plane parallel to and midway between said two parallel planes interrupting the path of travel of said internal cutting edge of said blade member at a midway point, said step of moving said workpiece in said radial direction to produce a wafer comprising effecting initial contact of said workpiece by said internal cutting edge of said blade member at said midway point of said path of travel of said internal cutting edge of said blade member, said step of detecting an axial load comprising detecting the operational axial load between said blade member at said midway point of said path of travel of said internal cutting edge of said blade member and said workpiece during said initial contact and correlating said operational axial load with the amount of flexure between said central portion of the blade member and said workpiece.

3. A method according to claim 2 wherein said step of correlating said operational axial load with the amount of flexure between said blade member and said workpiece comprises providing said correlation on a proportional basis.

4. A method according to claim 2 wherein said step of detecting the operational axial load comprises detecting the axial strain of said workpiece.

5. A method according to claim 4 wherein said step of detecting said axial strain of said workpiece comprises utilizing a strain gauge means to detect said axial strain.

6. A method according to claim 5 wherein said workpiece has a longitudinal axis, said rear longitudinal end of said workpiece having a base end surface perpendicular to the longitudinal axis of said workpiece, further comprising mounting said strain gauge means on said base end surface of said workpiece.

7. A method according to claim 2 wherein said step of detecting the operational axial load comprises holding the workpiece on a holder, and detecting the axial strain of said workpiece in said holder.

8. A method according to claim 7 wherein said step of detecting the axial strain of said workpiece comprises utilizing a strain gauge means, and further comprising mounting one part of said strain gauge means on said holder.

9. A method according to claim 1 wherein said workpiece has a longitudinal axis, said rear longitudinal end of said workpiece having a base end surface perpendicular to the longitudinal axis of said workpiece, said step of detecting said axial strain of said workpiece comprising mounting said axial load detecting means on said base end surface of said workpiece.

10. A method according to claim 1 wherein said workpiece has a cylindrical configuration, said step of rendering relative movement between the blade member and the workpiece comprising moving the workpiece in a radial direction to produce a wafer, said workpiece in moving in said radial direction traversing a swath path defined by two parallel planes spaced from one another a distance corresponding to the diameter of the workpiece said step of detecting the axial load acting between the workpiece and the blade member comprising detecting said axial load at a location disposed between said parallel planes.

11. A method for controlling the flexure of a blade member of a slicing machine in which a workpiece is placed in the blade member and in which the blade member is in the form of a flat ring, said workpiece having a forward longitudinal end and a rear longitudinal end, said blade member having an internal cutting edge on an internal periphery of the blade member, and wherein the blade member is rotated and relative movement is rendered between the rotated blade member and the workpiece in a radial direction of the blade member to produce a wafer from the forward longitudinal end of the workpiece, the controlling method comprising the steps of:

- disposing an axial load detecting means, at said rear longitudinal end of said workpiece with said axial load detecting means being generality axially aligned with said workpiece;
- detecting the axial load acting between the workpiece and the blade member;
- calculating the flexure amount of the blade member on the basis of the axial load; and
- correcting the flexure of the blade member on the basis of the flexure amount calculated.

12. A device for detecting the flexure of a blade member of a slicing machine in which a workpiece is placed in the blade member and in which the blade member is in the form of a flat ring, said workpiece having a forward longitudinal end and a rear longitudinal end, said blade member having an internal cutting edge on an internal periphery of the blade member, and wherein the blade member is rotated and relative movement is rendered between the rotated blade member and the workpiece in a radial direction of the blade member to produce a wafer from the forward longitudinal end of the workpiece, the detecting device comprising:

- a holder juxtaposed to said rear longitudinal end of said work piece;
- load detecting means generally axially aligned with said workpiece and disposed between said holder and said rear longitudinal end of said workpiece for detecting an axial load acting between the workpiece and the blade member; and
- flexure calculating means for calculating the flexure amount of the blade member on the basis of the axial load detected by the load detecting means.

13. A detecting device in accordance with claim 12, wherein the flexure calculating means comprises:

- memory means for storing a reference axial load detected by the load detecting means before the workpiece is brought into contact with the blade member or a reference flexure amount corresponding to the reference axial load detected; and
- comparing means for comparing the reference axial load or reference flexure amount stored in the memory means with a latest axial load detected by the load detecting means after the workpiece is brought into contact with the blade member or a latest flexure amount corresponding to the latest axial load detected to calculate an actual flexure amount on the basis of comparison result obtained by the comparing means.

14. A device according to claim 12 wherein said workpiece has a longitudinal axis, said rear longitudinal end of said workpiece having a base end surface perpendicular to the longitudinal axis of said workpiece, further comprising mounting means mounting said load detecting means on said base end surface of said workpiece.

15. A device for controlling the flexure of a blade member of a slicing machine in which a workpiece is placed in the blade member and in which the blade member is in the form of a flat ring, said workpiece having a forward longitudinal end and a rear longitudinal end, said blade member having an internal cutting edge on an internal periphery of the blade member, and wherein the blade member is rotated and relative movement is rendered between the rotated blade member and the workpiece in a radial direction of the blade member to produce a wafer from the forward longitudinal end of the workpiece, the controlling device comprising:

- a holder juxtaposed to said rear longitudinal end of said workpiece;
- load detecting means generally axially aligned with said workpiece and disposed between said holder and said rear longitudinal end of said workpiece for detecting an axial load acting between the workpiece and the blade member;
- flexure calculating means for calculating the flexure amount of the blade member on the basis of the axial load detected by the load detecting means; and
- the flexure calculating means comprising correcting means for correcting the flexure amount on the basis of the cutting force and the inclination between an axial direction of the blade member and an axial direction of the workpiece.

16. A control device in accordance with claim 15, wherein the load detecting means further detects a load acting in a direction normal to the axial load, and the correcting means of the flexure calculating means corrects the flexure amount on the basis of the load acting in the direction normal to the axial load.

17. A device for controlling the flexure of a blade member of a slicing machine in which a workpiece is placed in the blade member and in which the blade member is in the form of a flat ring, said workpiece having a forward longitudinal end and a rear longitudinal end, said blade member having an internal cutting edge on an internal periphery of the blade member, and wherein the blade member is rotated and relative movement is rendered between the rotated blade member and the workpiece in a radial direction of the blade member to produce a wafer from the forward longitudinal end of the workpiece, the controlling device comprising:

- a holder juxtaposed to said, rear longitudinal end of said workpiece;
- load detecting means generally axially aligned with said workpiece and disposed between said holder and said rear longitudinal end of said workpiece for detecting the axial load acting between the workpiece and the blade member; and
- flexure calculating means for calculating the flexure amount of the blade member on the basis of the axial load detected by the load detecting means, the flexure calculating means including correcting means for correcting the flexure amount on the basis of the weight of the workpiece and the inclination between an axial direction of the blade and an axial direction of the workpiece.

18. A control device in accordance with claim 17, wherein the load detecting means further detects the load acting in a direction normal to the axial load, and the correcting means of the flexure calculating means corrects the flexure amount on the basis of the load acting in the direction normal to the axial load.

19. A device for controlling the flexure of a blade member of a slicing machine in which a workpiece is placed in the blade member and in which the blade member is in the form of a flat ring, said workpiece having a forward longitudinal end and a rear longitudinal end, said blade member having an internal cutting edge on an internal periphery of the blade member, and wherein the blade member is rotated and relative movement is rendered between the rotated blade member and the workpiece in a radial direction of the blade member to produce a wafer from the forward longitudinal end of the workpiece, the controlling device comprising:

a holder juxtaposed to said rear longitudinal end of said workpiece;

load detecting means generally axially aligned with said workpiece and disposed between said holder and said rear longitudinal end of said workpiece for detecting the axial load acting between the workpiece and the blade member;

flexure calculating means for calculating the flexure amount of the blade member on the basis of the axial load detected by the load detecting means;

flexure adjusting means for correcting the flexure of the blade member; and control means for controlling the flexure adjusting means on the basis of the flexure amount calculated by the flexure calculating means.

\* \* \* \* \*